(12) United States Patent
Klee et al.

(10) Patent No.: US 9,592,469 B2
(45) Date of Patent: Mar. 14, 2017

(54) OXYGEN SEPARATION DEVICE FOR A PRESSURE SWING ADSORPTION SYSTEM

(71) Applicant: KONINKLIJKE PHILIPS N.V., Eindhoven (NL)

(72) Inventors: Mareike Klee, Straelen (DE); Rainer Hilbig, Aachen (DE); Robert William Murdoch, Kennesaw, GA (US); Achim Gerhard Rolf Koerber, Eindhoven (NL); Wilhelmus Cornelis Keur, Weert (NL); Paul Van Der Sluis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/416,066

(22) PCT Filed: Jul. 19, 2013

(86) PCT No.: PCT/IB2013/055939
§ 371 (c)(1),
(2) Date: Jan. 21, 2015

(87) PCT Pub. No.: WO2014/016746
PCT Pub. Date: Jan. 30, 2014

(65) Prior Publication Data
US 2015/0238895 A1 Aug. 27, 2015

Related U.S. Application Data

(60) Provisional application No. 61/675,380, filed on Jul. 25, 2012.

(51) Int. Cl.
*B01D 53/22* (2006.01)
*B01D 53/047* (2006.01)
(Continued)

(52) U.S. Cl.
CPC ......... *B01D 53/229* (2013.01); *A61M 16/101* (2014.02); *B01D 53/02* (2013.01);
(Continued)

(58) Field of Classification Search
CPC .... B01D 53/02; B01D 53/047; B01D 53/228; B01D 53/229; B01D 2053/221;
(Continued)

(56) References Cited

U.S. PATENT DOCUMENTS 5,938,822 A * 8/1999 Chen ...................... B01D 71/02
55/524
6,551,384 B1 4/2003 Ackley
(Continued)

FOREIGN PATENT DOCUMENTS

DE 10019695 A1 10/2001
EP 135069 * 3/1985 ............. B01D 13/04
(Continued)

OTHER PUBLICATIONS

Zhou Ming eet al., "Oriented Growth and Assembly of Zeolime Crystals on Substrates", Chinese Science Bulletin, Mar. 2008, vol. 53, No. 6, pp. 801-816.

*Primary Examiner* — Jason M Greene
(74) *Attorney, Agent, or Firm* — Michael W. Haas (57) ABSTRACT

The present invention refers to an oxygen separation device (12, 14) for a pressure swing adsorption system. In order to provide at least one of improved maintenance behavior, longer lifetime and improved energy consumption, the oxygen separation device (12, 14) comprises a gas inlet (18, 22) at a primary side for guiding a flow of oxygen comprising gas into the oxygen separation device (12, 14) and a gas outlet (28, 30) at a secondary side for guiding a flow of oxygen enriched gas out of the oxygen separation device (12, 14), an oxygen separation membrane (78) comprising
(Continued)

an oxygen separation sorbent being capable of separating oxygen from an oxygen comprising gas by sorbing at least one component of the oxygen comprising gas apart from oxygen, and a support structure (80) for supporting the oxygen separation membrane (78), wherein the support structure (80) comprises a plurality of support bars (82) being fixed to the oxygen separation membrane (78). The invention further relates to an oxygen separator (10) and to a method of generating an oxygen separation device (12, 14) for a pressure swing adsorption system.

15 Claims, 4 Drawing Sheets (51) Int. Cl.
  *B01D 69/10* (2006.01)
  *B01D 71/02* (2006.01)
  *A61M 16/10* (2006.01)
  *B01D 53/02* (2006.01)
  *B01J 20/18* (2006.01)
  *B01J 20/28* (2006.01)
  *C01B 13/02* (2006.01)
(52) U.S. Cl.
  CPC ......... *B01D 53/047* (2013.01); *B01D 53/228* (2013.01); *B01D 69/10* (2013.01); *B01D 69/105* (2013.01); *B01D 71/028* (2013.01); *B01J 20/18* (2013.01); *B01J 20/28033* (2013.01); *C01B 13/0255* (2013.01); *C01B 13/0259* (2013.01); *B01D 2053/221* (2013.01); *B01D 2253/108* (2013.01); *B01D 2253/25* (2013.01); *B01D 2256/12* (2013.01); *B01D 2257/102* (2013.01); *B01D 2259/4533* (2013.01); *B01D 2325/12* (2013.01); *C01B 2203/025* (2013.01); *Y10T 29/49789* (2015.01)
(58) Field of Classification Search
  CPC .... B01D 69/10; B01D 69/105; B01D 71/028; B01D 2256/12; B01D 2257/102
  USPC .................................................. 95/54; 96/11
  See application file for complete search history.

(56) References Cited

U.S. PATENT DOCUMENTS

| | | | | |
|---|---|---|---|---|
| 8,999,039 B2* | 4/2015 | Hilbig | ............... | B01D 53/228 95/130 |
| 2004/0060867 A1* | 4/2004 | Kriksunov | ............. | B01D 69/10 210/650 |
| 2004/0186018 A1* | 9/2004 | Carolan | ............... | B01D 53/228 502/303 |
| 2004/0245191 A1* | 12/2004 | Yagi | ..................... | B01D 53/228 210/791 |
| 2005/0006249 A1* | 1/2005 | Suzuki | ................. | B01D 53/228 205/633 |
| 2005/0061663 A1* | 3/2005 | Chen | ..................... | B01D 53/228 204/295 |
| 2005/0103710 A1* | 5/2005 | Sabottke | ................ | B01D 69/10 210/638 |
| 2007/0227358 A1* | 10/2007 | Takigawa | ............... | B01D 53/02 96/11 |
| 2009/0266237 A1 | 10/2009 | Serra Alfaro | | |
| 2010/0242734 A1* | 9/2010 | Maeda | ................. | B01D 53/047 96/110 |
| 2011/0042299 A1* | 2/2011 | Zhang | ..................... | B01D 69/10 210/490 |
| 2011/0300718 A1 | 12/2011 | Yan | | |
| 2014/0141225 A1* | 5/2014 | Petigny | ................ | B01D 71/024 428/220 |

FOREIGN PATENT DOCUMENTS

| | | | |
|---|---|---|---|
| EP | 135069 A2 | 3/1985 | |
| EP | 135069 A3 | 3/1985 | |
| WO | WO 2005009730 * | 2/2005 | ............. B01D 53/22 |
| WO | WO2005009730 A1 | 2/2005 | |
| WO | WO 2011/095920 A1 * | 8/2011 | ............. B01D 71/02 |
| WO | WO2011095920 A1 | 8/2011 | |
| WO | WO 2011/107898 A1 * | 9/2011 | ............. B01D 53/22 |
| WO | WO2011107898 A1 | 9/2011 | |
| WO | WO 2012/052915 * | 4/2012 | ............. B01D 53/22 |
| WO | WO2012-52915 A1 | 4/2012 | |

* cited by examiner

OXYGEN SEPARATION DEVICE FOR A PRESSURE SWING ADSORPTION SYSTEM

CROSS-REFERENCE TO RELATED APPLICATIONS

This patent application claims the priority benefit under 35 U.S.C. §371 of international patent application no. PCT/IB2013/055939, filed Jul. 19, 2013, which claims the priority benefit under 35U.S.C §119(e) of U.S. Provisional Application No. 61/675,380 filed on Jul. 25, 2012, the contents of which are herein incorporated by reference.

FIELD OF THE INVENTION

The invention relates to the field of oxygen separation. More particularly, the invention relates to the field of oxygen separation by pressure swing adsorption. In detail, the invention refers to an oxygen separation device for a pressure swing adsorption system, to an oxygen generator comprising such an oxygen separation device and to a method of generating an oxygen separation device for a pressure swing adsorption system.

BACKGROUND OF THE INVENTION

Oxygen generation, or oxygen separation, respectively, plays an important role in different application areas, covering for example the generation of high purity oxygen, and partial oxidation reactions of hydrocarbons in reactors. The production of high purity oxygen is also of particular interest for small, low noise oxygen generators for medical applications such as home healthcare applications.

Oxygen therapy, for example, is the administration of oxygen as a therapeutic modality. Oxygen therapy benefits the patient by increasing the supply of oxygen to the lungs and thereby increasing the availability of oxygen to the body tissues. The main homecare application of oxygen therapy is for patients with severe chronic obstructive pulmonary diesease (COPD), a disease that effects more than 13 million patients in the US, for example.

For on-demand generation of oxygen, commercial solutions, so-called oxygen concentrators are known. Philips Respironics, for example, is offering a family of oxygen concentrator products for patients requiring oxygen therapy at home (EverFlo) and on the move (EverGo). Such systems may be based on a pressure swing adsorption process.

Such a pressure swing adsorption process is further known from U.S. Pat. No. 6,551,384 B1, for example. This document discloses a pressure swing adsorption method using a two-bed apparatus. Such a method comprises the following steps: simultaneous feed and product pressurization; adsorption; equalization; evacuation; evacuation and purge; simultaneous equalization and feed.

There is, however, still the need for improvements especially regarding an on-demand generation of oxygen.

SUMMARY OF THE INVENTION

It is an object of the invention to provide an oxygen separation device for a pressure swing adsorption system that provides at least one of improved maintenance behavior, longer lifetime and improved energy consumption.

This object is achieved by an oxygen separation device according to claim 1 and by an oxygen separator according to claim 11. This object is furthermore achieved by a method of generating an oxygen separation device for a pressure swing adsorption system according to claim 13. Preferred embodiments may be derived from the dependent claims.

An oxygen separation device for a pressure swing adsorption system comprises a gas inlet at a primary side for guiding a flow of oxygen comprising gas into the oxygen separation device and a gas outlet at a secondary side for guiding a flow of oxygen enriched gas out of the oxygen separation device, an oxygen separation membrane comprising an oxygen separation sorbent being capable of separating oxygen from an oxygen comprising gas by sorbing at least one component of the oxygen comprising gas apart from oxygen, and a support structure for supporting the oxygen separation membrane, wherein the support structure comprises a plurality of support bars being fixed to the oxygen separation membrane.

The term oxygen separation device may particularly refer to the active part of an oxygen separator. It may for example comprise an oxygen separation sorbent which may interact with an oxygen comprising gas, or with defined constituents of the latter, and may thus separate oxygen from the oxygen comprising gas by means of interaction with at least one constituent of the oxygen comprising gas apart from oxygen. Consequently, the oxygen separation device as such, or its oxygen separation sorbent, respectively, is capable of separating oxygen from an oxygen comprising gas particularly by sorption processes, such as adsorption processes. It may exemplarily be formed as a compact device being arranged in, or comprises a housing.

The expression pressure swing adsorption system may particularly refer to an oxygen separation system which produces pure or essentially pure oxygen by means of sorption processes, or adsorption processes, respectively. By usage of such a system at least one component of an oxygen comprising gas is sorbed to a sorbent whereas oxygen is not or less bound to the sorbent material and thus may be separated from the sorbed components. In order to remove the sorbed substance or substances, the sorbent material is provided with a gas flow in the reversed direction, particularly by reversing the pressure behavior upstream and downstream the sorbent, and thus by a pressure swing.

The term oxygen separator as used herein may particularly refer to a device which is capable of separating oxygen from an oxygen comprising gas. Consequently, by means of an oxygen separator, starting from an oxygen comprising gas, pure or essentially pure oxygen or at least oxygen enriched gas may be generated.

Furthermore, the term primary side of the oxygen separation device, as used herein, may refer to the side or the part of the oxygen separation device being directed towards the direction, at which the oxygen comprising gas is guided to the oxygen separation device, whereas the term secondary side of the oxygen separation device, as used herein, may refer to the side or the part of the oxygen separation device being directed towards the opposite side, i.e. to the side at which the generated pure oxygen or oxygen enriched gas is present.

Additionally, the term oxygen comprising gas, as used herein, may refer to any gas which at least partly comprises gaseous oxygen, or which consists of oxygen. The term oxygen enriched gas shall thereby particularly mean a gas which has a higher concentration with respect to oxygen compared to the oxygen comprising gas and which may in an extreme case be pure oxygen.

An oxygen separation membrane may furthermore be understood in the sense of the present invention as a layer, particularly as a flat layer, for example in the sense of a thin film structure, comprising the oxygen separation sorbent and thus being mainly responsible for achieving the oxygen separation effect by means of sorption processes, or adsorption processes, respectively.

The term support bar further refers to a structure supporting the oxygen separation membrane but being spatially restricted and thus has a smaller dimension with respect to the oxygen separation membrane. Due to the fact that a plurality, i.e. two or more than two, support bars are provided, a flowing path for the oxygen comprising gas, or the oxygen enriched gas, respectively, is provided between the support bars. Additionally, it may be preferred that the support bars have no contact with each other.

An oxygen separation device like described above may particularly provide improved maintenance behavior, less energy consumption, improved lifetime as well as improved mass-transfer and heat-transfer behavior in an oxygen separation process by means of a pressure swing adsorption system.

In detail, due to the fact that the active part being responsible for oxygen separation is formed by a membrane and thus in a particularly thin layered form, potential disadvantages being known from arrangements known in the art, such as particularly of sieve beds comprising adsorption beads, like known for pressure swing adsorption systems may be overcome.

For example, by using a membrane structure for oxygen separation like described above, significant advantages with respect to heat-transfer and mass-transfer properties may be achieved. This is due to the fact that for pressure swing adsorption systems, traditionally used sorbents are used in form of beads or extrudates arranged in large adsorption beds. The rate of mass-transfer is determined by the diffusion path in the crystals. However, in pressure swing adsorption processes, there may be a trade-off between heat-transfer and mass-transfer limitations. In case the used beads have an increasing diameter, the pressure drop may be reduced, but deteriorated mass-transfer and heat-transfer limitations may occur. Consequently, the size of the beads in the sieve beds are traditionally used dependent from the used processes and conditions. Smaller beads show increased mass-transfer but a disadvantage is that the beads are showing abrasion at the container walls, or the housing, respectively, which may result in dust particles from the bead. This abrasion can result in reduced lifetime of the respective sieves. The small particles resulting from abrasion may furthermore close the filters being present at the gas inlet and the gas outlet, respectively, which may significantly reduce the performance of the system or even limit the operation of the system. Furthermore, the small particles resulting from abrasion may strongly effect the pressure distribution in the traditional sieve bed.

As a result, by using a membrane structure, for example as a thin film, the disadvantages of sieve beds comprising adsorbates in the form of beads, i.e. increased mass-transfer and heat-transfer limitations with large beads and increased abrasion at container walls with small beads may be overcome.

By using a membrane such as a thin film as active oxygen separation part, it is enabled to provide small particles with a large surface area resulting in an improved mass-transfer with respect to bulk beads. Therefore, a high oxygen separation capacity may be enabled. Thereby, the particles, or the sorbent, respectively, are fixed or sticked in a defined layer, particularly stable as such, on a support structure and are thus not removed at least at usual working conditions, consequently no abrasion takes place in the membrane such, that abrasion can be prevented or at least significantly reduced. Consequently, next to improved mass-transfer limitations, the formation of dust or extremely small particles may be prevented resulting in significantly improved performance of oxygen separation and significantly reduced damaging behavior of the oxygen separation device, respectively. Consequently, the lifetime as well as the maintenance behavior of an oxygen separation device like described above may be significantly improved.

Apart from that and due to the fact that the support structure comprises a plurality of support bars being fixed to the oxygen separation membrane either directly or indirectly via a further layer, the contact of the membrane to further components of the oxygen separation device may be reduced. Consequently, heat-transfer limitations are improved resulting in a more energy efficient working behavior. It is thereby obvious that the feature of the support bars being fixed to the membrane may be dependent from the method of producing this arrangement and may as well be understood as the membrane being fixed to the support bars. Due to the fact that no continuous support layer is provided but the support is achieved by a plurality of support bars, i.e. at least two or preferably more than two support bars, the pressure drop can be hold in minimal ranges due to the fact that a well defined open structure of the support structure is provided enabling an advantageous and well defined gas exchange and contact of the oxygen comprising gas with the membrane.

Thereby, the outer support bars may act as a kind of housing, wherein the inlet between the support bars may act as gas inlet and the opposite side of the membrane may act as outlet, or vice versa for example, so that the provision of a housing may under circumstances be omitted.

According to an embodiment the oxygen separation sorbent comprises a zeolite material. Especially zeolite materials are effective sorbents for separating oxygen from nitrogen thereby sorbing nitrogen, for example, so that the oxygen comprising gas may be air. The oxygen separation device may thus be operated in a safe and cost-saving manner. Apart from that, no gas cylinders including the oxygen comprising gas may be stored so that the maintenance behavior is further improved. Further, especially with respect to zeolite materials, small particles may be fixed on a support structure comprising a plurality of support bars and are thus especially useful for an oxygen separation device according to the present invention. Thereby, clay binders may be omitted so that the mass-transport behavior may be further improved. In a non-limiting example, a crystalline zeolite material layer having the composition $M^{n+}_{x/n}[(AlO_2)^-_x(SiO_2)]_y$ with M being an alkaline ion or an earth alkaline ion, wherein $^{n+}$ is the charge of the cation M and may be 1 or 2. The ratio y/x is equal to 1 or larger than 1. As an example the zeolite material could be a Li exchanged Low Silica X zeolite with a ratio y/x between 1 to 1.5.

According to a further embodiment the support bars comprise silicon (Si), glass, ceramic such as an aluminium oxide, glass ceramic, metal, or one or more combinations of one or more of the afore-mentioned materials. For example, the support bars may consist of one or more of the afore-mentioned materials such as particularly of silicon. This embodiment allows generating a well defined and highly pure flow of oxygen due to the fact that these materials shows no or nearly no interactions with an oxygen comprising gas, so that no undesired side products may appear deteriorating the membrane or the generated flow of pure or essentially pure oxygen. Apart from that, the afore-mentioned materials such as particularly silicon may be machined with micro patterning processes for example known from semiconductor products allowing generating a well defined support structure and thus a well defined oxygen separation behavior even for very small dimensions. These kind of materials further exhibit a sufficiently high stability for supporting the membrane, especially if the membrane is formed very thin.

According to a further embodiment a layer is provided at least at one end of the support bars, the layer comprising silicon dioxide, silicon nitride, a combination of the afore-mentioned materials, or a spin-on glass layer. For example, such a layer may be provided between the support bars and the membrane or at the opposite end of the support bars, or at both afore-mentioned positions. Especially when being provided between the flowing paths it may be locally restricted. A locally restricted layer may thereby particularly mean a layer which is present adjacent to or on the support bars, respectively but which is not or not essentially present in the region of the flowing paths being generated between the respective support bars. Such a layer comprising silicon oxide or silicon nitride or mixtures thereof or a spin-on glass layer may particularly function as a layer which may help to fix the membrane to the substrate and may thus act as an adhesion promoter. Such a layer may thus improve the stability of the oxygen separation device, further improving the lifetime and the maintenance behavior. Additionally, if provided at the side of the support bars being located opposite of the membrane, a layer according to this embodiment may help forming or shaping, respectively, the bars and the respective flowing paths in the desired manner, thereby acting as a mask, for example. In particular, the layers can be dense or porous and can be applied by any deposition technique, for example thermal oxidation or chemical vapor deposition. A silicon nitride layer may preferably be applied by chemical vapor deposition. A spin-on glass layer, for example, may be known from semiconductor devices. The thickness of the silicon nitride, silicon oxide, or spin-on glass layer, respectively, preferably has a thickness in the range between $\geq 100$ nm and $\leq 100$ μm, preferably between $\geq 100$ nm and $\leq 10$ μm.

According to a further embodiment the support bars comprise a porous material. For example, the support bars may consist of a porous material. The provision of a porous materials for the support bars allows the gas flux from the inlet of the oxygen separation device to the oxygen separation membrane to be further improved due to the fact that the oxygen comprising gas may flow to the oxygen separation membrane through the flowing paths being generated between the support bars, but may furthermore flow through the support bars, or through its porous structure, respectively. Consequently, the oxygen comprising gas may as well flow through the oxygen separation membrane in the region adjacent to the support bars.

According to a further embodiment a plurality of oxygen separation membranes and thus two or more oxygen separation membranes are provided, wherein one oxygen separation membrane is located downstream a further oxygen separation membrane. This embodiment allows providing an especially improved gas separation capacity allowing high gas fluxes and an especially long lifetime, for example. Apart from that, the maintenance behavior is especially improved according to this embodiment due to the fact that even if one membrane is damaged, fully loaded with sorbed material, or does not work appropriate, one or more further oxygen separation membranes will provide the desired oxygen separation procedure. Apart from that, the oxygen separation membranes may be formed very thin due to the fact that the oxygen separation performance may be shared by a plurality of oxygen separation membranes thereby allowing providing enough sorbent material for the required oxygen separation process. Generally, according to this embodiment, two membranes may be provided or even more than two, for example in the range of 5 to 10 membranes, or even more may be provided. The plurality of oxygen separation membranes may be connected by a plurality of support bars, or they could also be loosely stacked on top of each other, thereby for example being fixed at the sides to a housing, for example.

According to a further embodiment the support bars have a length of $\geq 50$ μm. For example, the support bars have a length of $\geq 50$ μm to $\leq 1000$ μm. The length may thereby be defined as the distance which lies between the beginning of the support bars before reaching the adjacent component, particularly the oxygen separation membrane or an additional layer, such as the silicon dioxide layer, for example, and in the flow direction of the oxygen comprising gas. According to this embodiment, it is well possible to form the oxygen separation device in very small dimensions being particularly suitable for portable homecare devices. This may be the case when providing one oxygen separation membrane or a stack of a plurality of membranes one after the other in the flow direction of the oxygen comprising gas with support bars being arranged there between, thereby anyhow achieving very compact dimensions. Consequently, this embodiment may under circumstances be especially preferred with respect to homecare devices. Apart from that, such support bars show a sufficient stability for supporting the membrane to ensure that the risk of cracks or damages to be formed is minimized.

According to a further embodiment the oxygen separation membrane has a thickness of $\geq 1$ μm to $\leq 500$ μm. This allows the flux of oxygen passing the membrane to be increased as the thickness of the membrane may under circumstances have a major influence to the permeability of the latter. As the membrane systems according to the invention can be produced on equipment usually applied for the production of semiconductor devices, low cost productions are possible. Additionally, the membrane system according to the invention can be applied in small, flat devices which are of relevance for applications such as medical applications, particularly in the field of home care. Consequently, by forming the membrane in a thickness in a range of $\geq 1$ μm to $\leq 500$ μm, particularly $\geq 1$ μm to $\leq 30$ μm, the permeability and thus the gas flux of the membrane system may be increased allowing, for example, providing high efficient and small oxygen separation devices.

According to a further embodiment the oxygen separation membrane comprises zeolite crystallites, or zeolite particles, or zeolite beads, particularly as sorbent material. Making use of thin film processes zeolite crystallites grown next to each other may be present. They can form a fine-grained zeolite membrane. Fine grained zeolite membranes are especially achieved when deposition methods are used that realize thin, dense zeolite films such as spin-on processing, or sputtering where also a high temperature process could be applied. Alternatively the zeolite membranes can comprise of zeolite particles, which according to the invention may particularly comprise or consist of small zeolite crystallites. Zeolite membranes with particles may for example be realized in deposition techniques where films with a lower density are deposited such as spin-on processing and low temperature treatment or printing. Dependent on the deposition technique and the temperature applied in the process the zeolite films can be formed from zeolite crystals or grains or particles in a dense or a porous layer. The zeolite layer can in this embodiment comprise zeolite crystals or grains or particles that have dimensions of more or equal to 10 nm up to several tens of micrometer, such as 30 µm, for example. They can be realized by applying the zeolite layers by e.g. thin film processing technologies such as spin-on processing, hydrothermal processing or any other film technology. Alternatively it is also possible that the oxygen separation membrane is built up from agglomerates of zeolite crystals, or zeolite particles, respectively. The agglomerates of zeolite crystals or particles are called beads. These agglomerates of zeolite crystals also called beads can be realized in either a dense or porous arrangement to form the membrane. For realization of the zeolite membranes e.g. printing technologies can be used. The beads or agglomerates, respectively, can have diameters of several micrometer, such as of 3 µm up to several tens of micrometer e.g. 30 µm or even larger. Particularly in this case, the thickness of the membrane may exceed the non-limiting value of 500 µm. This embodiment allows providing zeolite material like known from traditional oxygen separation devices such as pressure swing adsorption systems. The realization of the zeolite material fixed in the membrane enables that no abrasion of the zeolite can occur and thus contamination with particles in the zeolite bed is prevented. Consequently, according to these embodiments the advantages of fine grained zeolite material with respect to heat-transfer as well as mass-transfer behavior may be reached without the respective disadvantages with respect to abrasion of very small particles like described above.

According to a further embodiment the oxygen separation membrane together with the support structure is mounted in a housing. This is an especially easy and cost-saving manner to generate the oxygen generation device. In detail, in case the membrane together with the support is enclosed in a housing, wherein a gas inlet as well as a gas outlet are formed in said housing, the oxygen comprising gas may easily be guided into the housing and to the primary side of the oxygen separation membrane and furthermore from the secondary side of the oxygen separation membrane out of the housing. Thereby, an undesired interaction between the oxygen separation membrane and the outer atmosphere may easily be prevented leading to especially defined conditions inside the housing and thus at the oxygen separation membrane. Especially, the oxygen separation behavior may as well be especially defined. Apart from that, deterioration of the oxygen separation behavior due to the influence of oxygen from the atmosphere surrounding the oxygen separation device may be inhibited so that the maintenance behavior as well as the lifetime of such an oxygen separation device may further be improved.

With respect to further technical features as well as advantages of the oxygen separation device according to the invention it is referred to the description of the oxygen separator, the method for generating an oxygen separation device and the figures.

The invention further relates to an oxygen separator, comprising at least one oxygen separation device like described above and thus with one or more of the aforementioned features, and a pressure adjusting device for creating a pressure difference between the primary side and the secondary side of the oxygen separation device. The term pressure adjusting device may refer to any device which is capable of generating a pressure difference between the primary side and the secondary side of the oxygen separation device. It may for example be a gas compression device being connected to the primary side of the oxygen separation device, or a vacuum pump being connected to the secondary side of the oxygen separation device.

An oxygen separator like defined above thus comprises at least one oxygen separation device. It may thus comprise only one oxygen separation device or a plurality of two or more than two oxygen separation devices and may generally form a pressure swing adsorption system (PSA system). For example, the oxygen separator may comprise two oxygen separation devices being arranged in parallel. However, dependent from the desired application, even more than two oxygen separation devices may be arranged in parallel. As an example, all oxygen separation devices present may be arranged in parallel.

Such an oxygen separator allows significant improvements with respect to maintenance behavior and lifetime, for example. In detail, the contamination behavior due to small particles being generated by abrasion may be reduced. Apart from that, the mass-transfer behavior as well as the heat-transfer behavior may significantly be improved.

With respect to further technical features as well as advantages of the oxygen separator according to the invention it is referred to the description of the oxygen separation device, the method for generating an oxygen separation device and the figures.

The invention further relates to a method of generating an oxygen separation device for a pressure swing adsorption system like described above, said method comprising the steps of: providing a substrate, particularly in the form of a substrate layer; providing a membrane onto the substrate; and processing the substrate by forming a plurality of substrate bars out of the substrate.

Such a method is a very cost-saving and easy process for generating an oxygen separation device which is capable of improving at least one of heat-transfer behavior, mass-transfer behavior, lifetime and maintenance behavior. Furthermore, according to this method an arrangement may be provided comprising a membrane which is fixed to support bars having especially defined dimensions and geometries. For example, this method is suitable for providing a thin film molecular sieve system where small adsorbent particles, such as zeolite crystallites, are processed on a carrier such as a silicon carrier.

In detail, in a first step, a substrate is provided. The substrate may be formed as a layer and may for example comprise or be formed from silicon with a suitable thickness. The thickness chosen may define the length of the substrate bars being generated at a later step and may lie in a range of $\geq 50$ µm to $\leq 1000$ µm. The substrate material may further be porous or not.

According to a further step, a membrane is provided onto the substrate. The membrane particularly comprises a sorbent material for separating oxygen from an oxygen comprising gas. For example, a zeolite material, such as one comprising a Faujasite crystal lattice may be deposited onto the substrate layer as sorbent material like described above. In detail, this may be realized, for example, by means of a sol-gel process using spin on processing and/or spray deposition, preferably resulting in a thickness in a range of $\geq 1$ µm to $\leq 500$ µm. For example, heating in a furnace or a hydrothermal process may be used. But also other deposition techniques such as printing or evaporation techniques such as chemical vapor deposition techniques can be used. The sorbent material, such as the zeolite material, may be present in the membrane layer in form of small crystallites, or particles, or in the form of agglomerates, or beads, respectively. Thin film deposition techniques such as spin-on processing enable fine-crystallized zeolite layers with crystal sizes of 10 nm up to several micrometer. But also by using e.g. printing technologies sorbent material in form of beads up to several tens of micrometer can be realized.

In a further step, the substrate is processed by forming a plurality of substrate bars out of the substrate. This step may be realized, for example, by processes generally known in the semiconductor processing in particular in case the substrate comprises silicon.

In a further optional step, the so formed arrangement may be fixed in a housing, the housing preferably comprising a gas inlet and a gas outlet. It may thereby be preferred that the bars are arranged in the flow direction of the oxygen comprising gas and thus that the membrane is arranged rectangular to that flow direction in order to generate a superior flux of gas. Further, the support bars may be directed towards the primary side of the oxygen separation device. This could support to guide the flow to the membranes in a very defined manner. But also a positioning in the opposite direction could be possible. Thereby, only one arrangement comprising a plurality of support bars and a membrane may be provided inside the housing, or more than one respective arrangements may be provided one downstream the other.

According to an embodiment a layer comprising silicon oxide or silicon nitride or a combination of silicon oxide and nitride or a spin-on glass layer is applied to at least a part of the substrate. This embodiment allows generating a layer provided between the support bar and the membrane or at the opposite end thereof, or at both afore-mentioned positions. Such a layer, for example comprising silicon oxide, may particularly function as a layer which may help to fix the membrane to the substrate and may thus act as an adhesion promoter. Such layer could alternatively also remain underneath the membrane and such as well in the region of the flowing paths. Such a layer may thus improve the stability of the oxygen separation device, further improving the lifetime and the maintenance behavior. Additionally, if provided at the side of the bar being located opposite of the membrane, a layer according to this embodiment may help forming or shaping, respectively, the bars and the respective flowing paths in the desired manner, thereby acting as a mask, for example. In particular, the layers can be dense or porous and can be applied by any deposition technique, for example thermal oxidation or chemical vapor deposition. A silicon nitride layer may be applied by any deposition technique, for example chemical vapor deposition. A silicon oxide layer may be realized by thermal oxidation. A spin-on glass layer as such is known from traditional semiconductor processes. The thickness of the silicon nitride, or silicon oxide layer, respectively, or of the spin-on glass layer preferably has a thickness in the range between ≥100 nm and ≤100 μm, preferably between ≥100 nm and ≤10 μm.

According to a further embodiment the substrate is processed by micro-machining such as silicon micro-machining or sandblasting. According to this embodiment the support bars are formed in a very defined way even if they are formed in very small dimensions. Correspondingly, the flowing paths between said support bars are formed very defined leading to a very defined working behavior, or oxygen separation behavior, respectively, of the oxygen separation device. This embodiment may be especially preferred in case the support bars comprise silicon.

With respect to further technical features as well as advantages of the method for generating an oxygen separation device according to the invention it is referred to the description of the oxygen separation device, the oxygen separator and the figures.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
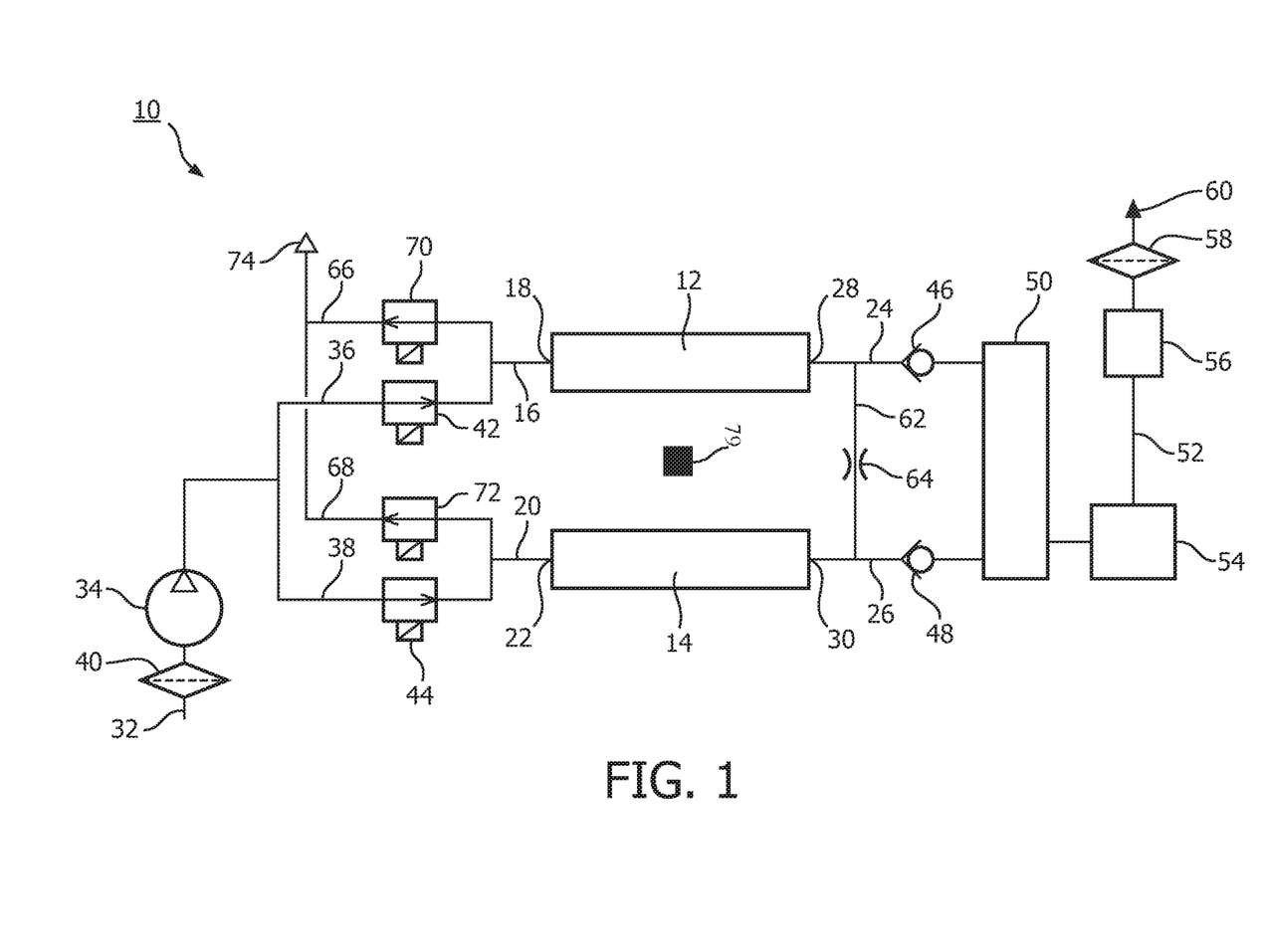
FIG. 1 shows a pressure swing adsorption system.

In FIG. 1, an oxygen separator 10 for generating oxygen is schematically shown. The oxygen separator 10 is formed as a pressure swing adsorption system and may be used for generating oxygen with respect to therapeutic applications, for example in the field of COPD treatment. The oxygen separator 10 may be designed as a stationary arrangement, for example for using it in a hospital, or it may be a portable device, for example for using it in the field of homecare applications. However, the oxygen separator 10 may furthermore be used for any application at which pure or essentially pure oxygen has to be provided, for example in air planes or for welding purposes. Such an oxygen separator 10, or oxygen concentrator, respectively, may be based on an oxygen concentrator such as the one called EverGo and which is purchasable from Philips Respironics.

The oxygen separator 10 comprises at least one oxygen separation device 12 which is capable of separating oxygen from an oxygen comprising gas. However, it is preferred that the oxygen separator 10 comprises at least two oxygen separation devices 12, 14, wherein at least two or more than two oxygen separation devices 12, 14 are arranged in parallel. In the following, the invention is described with respect to two oxygen separation devices 12, 14. However, it is clear for one skilled in the art that every feature may be provided correspondingly by using just one oxygen separation device 12 or more than two oxygen separation devices 12, 14. Each oxygen separation device 12, 14 may be equipped with an oxygen separation sorbent like will be apparent down below. The oxygen separation sorbent is particularly configured for letting oxygen pass at least in a large amount without significantly impeding its flow, but for interacting with, or sorbing, respectively other components being present in an oxygen comprising gas. In case air is used as oxygen comprising gas, it is thus preferred that the oxygen separation sorbent is configured for sorbing nitrogen, or adsorbing nitrogen, respectively. Suitable oxygen separation sorbents may comprises a zeolite material such as a lithium zeolite material. However it may be possible to use every suitable oxygen separation sorbent known in the art, for example for use in pressure swing adsorption processes.

An inlet conduct 16 is provided for guiding a flow of oxygen comprising gas to the gas inlet 18 of the oxygen separation device 12 at its primary side. Correspondingly, an inlet conduct 20 is provided for guiding a flow of oxygen comprising gas to the gas inlet 22 of the oxygen separation device 14 at its primary side, respectively. Furthermore, outlet conducts 24, 26 for guiding oxygen enriched gas, or pure oxygen, respectively, out of the oxygen separation devices 12, 14 are connected to gas outlets 28, 30 of the respective oxygen separation device 12, 14.

The inlet conducts 16, 20 of the oxygen separation devices 12, 14 are connected to an inlet 32 of the oxygen separator 10. Connected to the inlet 32 may be a source of oxygen comprising gas, such as a gas storing device or the air surrounding the oxygen separator 10. Additionally, a pressure adjusting device for creating a pressure difference between the primary side and the secondary side of the oxygen separation device 12, 14 may be provided. According to FIG. 1, a compressor 34 is provided for compressing the oxygen comprising gas and forcing it through the inlet conducts 36, 38, which may be part of or connected to the inlet conducts 16, 20, to the oxygen separation devices 12, 14. Downstream or upstream the compressor 34, an inlet filter 40 may be provided in order to provide a first cleaning step of the oxygen comprising gas. In detail, especially solid particles may be filtered out of the oxygen comprising gas.

In order to allow the oxygen comprising gas to be guided through the oxygen separation devices 12, 14 intermittently, inlet valves 42, 44 may be provided in the inlet conducts 36, 38. A valve according to the invention shall be any device which may allow a gas flow, inhibit a gas flow and/or regulate the amount of a gas flow. Consequently, by closing the valve 44 and by opening the valve 42, the oxygen comprising gas may be guided through the first oxygen separation device 12, whereas the oxygen comprising gas may be guided through the second oxygen separation device 14 by opening the valve 44 and by closing the valve 42. Correspondingly, a valve 46, such as a check valve, may be provided in the outlet conduct 24 and a valve 48, such as a check valve, may be provided in the outlet conduct 26. By guiding the oxygen comprising gas through the first oxygen separation device 12, the valve 46 may be opened whereas the valve 48 may be closed. Correspondingly, by guiding the oxygen comprising gas through the second oxygen separation device 14, the valve 48 should be opened whereas the valve 46 should be closed.

Downstream the valves 46, 48, the outlet conducts 24, 26 are connected to an oxygen accumulator 50, or a gas tank, respectively, in order to store the generated oxygen. The oxygen accumulator 50 may be connected to an outlet line 52 in which a flow controller 54 may be provided in order to control a stream of pure oxygen. Apart from that, a purity sensor 56 may be provided in the outlet line 52 in order to monitor the purity of the generated oxygen. Furthermore, an additional filter 58 may be provided in the outlet line 52 before the generated oxygen is guided to an outlet 60. From the outlet 60, the generated oxygen enriched gas may be guided to the desired application, such as to a patient.

The outlet conduct 24 of the first oxygen separation device 12 and the outlet conduct 26 of the second oxygen separation device 14 may be connected by a cross conduct 62 upstream the valves 46, 48, in which a flow regulator 64, such as an orifice or a flow controller, may be provided. This allows guiding a defined part of the generated oxygen, for example generated in the oxygen separation device 12, 14, back through the further oxygen separation device 14, 12, or vice versa, for purging purposes and thus for regenerating the oxygen separation devices 12, 14. With this regard, purging lines 66, 68 are provided at the primary sides of the oxygen separation devices 12, 14, each comprising a valve 70, 72. If oxygen is guided through the oxygen separation devices 12, 14, from their secondary side to their primary side for regeneration purposes, the outflow may then be guided selectively through the purging lines 66, 68 and through an exhaust 74.

Furthermore, a heating device 79 for heating the oxygen separation device 12, 14 may be provided. The heating device 79 may act on the whole oxygen separation device 12, 14 or may only heat special regions thereof. In general, every heating device 79 known in the art may be used. For example, heating coils may be provided.

A detailed view of embodiments of the oxygen separation device 12, 14 are shown in FIGS. 2 to 6. With this regard, the same or comparable components may be defined by the same reference signs in order to simplify the respective description.

Figure 2:
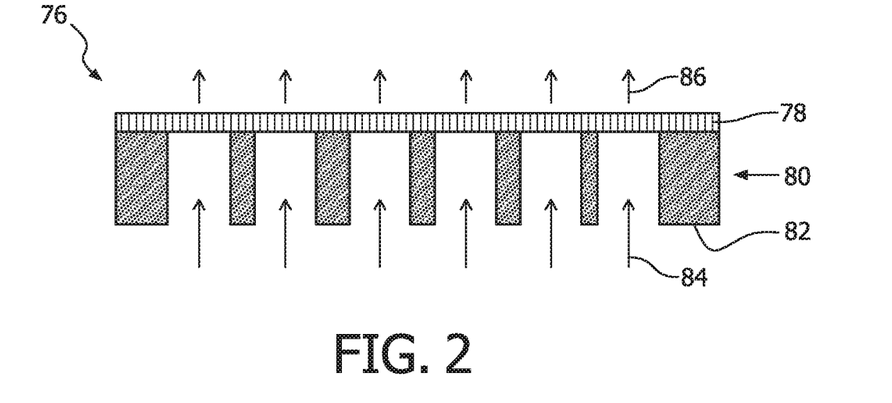
FIG. 2 shows an embodiment of an oxygen separation device according to the invention.

According to FIG. 2 an embodiment of an arrangement 76 is shown, which may for or be part of the oxygen separation device 12, 14. Such an arrangement 76 comprises an oxygen separation membrane 78 comprising an oxygen separation sorbent being capable of separating oxygen from an oxygen comprising gas by sorbing at least one component of the oxygen comprising gas apart from oxygen. The oxygen separation sorbent may comprise a zeolite material, such as zeolite crystallites, or zeolite particles, or zeolite beads like will be apparent down below. For example, the membrane 78 may comprise a fine zeolite layer having the composition $M^{n+}_{x/n}[(AlO_2)^-_x(SiO_2)]_3$ with M being a alkaline ion or an earth alkaline ion, wherein $^{n+}$ is the charge of the cation M and may be 1 or 2. The ratio y/x is equal to 1 or larger than 1. As an example the zeolite material could be a Li exchanged Low Silica X zeolite with a ratio y/x between 1 to 1.5. Furthermore, the membrane 78 may have a thickness of $\geq 1$ µm to $\leq 500$ µm and/or an exemplary width of the membrane 78 between the support bars 82 and thus a width of the flowing paths of exemplary and non limiting $\geq 500$ µm to $\leq 5$ mm. According to these exemplary and non-limiting values, a fine crystalline zeolite layer with especially large surface area for gas exchange may be realized.

The arrangement 76 further comprises a support structure 80 for supporting the oxygen separation membrane 78, wherein the support structure 80 comprises a plurality of support bars 82 being fixed to the oxygen separation membrane 78 and formed, for example, from a standard support, such as a silicon wafer, having a thickness of $\leq 1000$ µm, or the wafer can have decreased thickness, for example polished down, resulting in a thickness of the substrate and thus a length of the support bars 82 is $\geq 50$ µm. In this way, the fine oxygen separation sorbent is fixed on the support allowing that no small particles due to abrasion are formed. Further, the support bars 82 may in a non-limiting embodiment be formed straight.

The arrangement 76 comprising the support structure 80 as well as the support bars 82 may itself form the oxygen separation device 12, 14. In this case, a gas inlet 18, 22 for guiding a flow of oxygen comprising gas into the oxygen separation device 12, 14 may be formed at the end of the support bars 82 at their side opposite to the oxygen separation membrane 78 and the gas outlet 28, 30 may be formed at the secondary side of the membrane 78. However, it may be preferred that the membrane 78 together with the support structure 80 is mounted in a housing such as a cylinder, for example formed from aluminium not shown as such. In the latter case, the housing may be provided with respective openings particularly functioning as further a gas inlet 18, 22 and a gas outlet 28, 30, respectively.

It is indicated that an oxygen comprising gas is guided to the oxygen separation membrane 78 by means of the arrows 84. The oxygen comprising gas will then interact with the oxygen separation membrane 78, or its oxygen separation sorbent, respectively. As a result, a flow of pure or essentially pure oxygen is generated which is indicated by the arrows 86 and which may flow out the outlet 28, 30 into the outlet conduit 24, 26 to its application.

Figure 3:
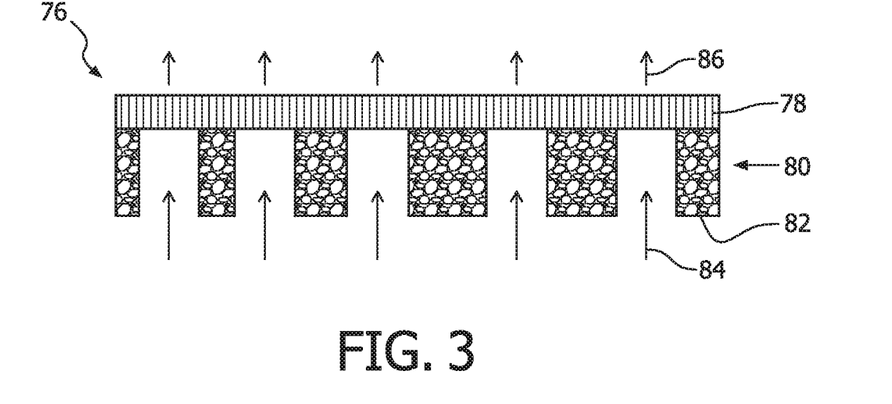
FIG. 3 shows a further embodiment of an oxygen separation device according to the invention.

FIG. 3 shows a further embodiment of an arrangement 76. Comparable to FIG. 2, the arrangement 76 comprises an oxygen separation membrane 78 and a support structure 80 comprising a plurality of support bars 82. According to FIG. 3, however, the support bars 82 are formed from a porous material, which could be for example a porous ceramic material or a porous metal substrate.

Figure 4:
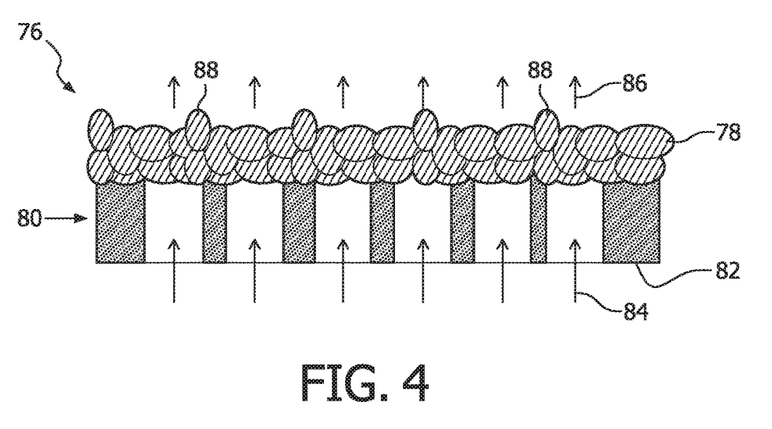
FIG. 4 shows a further embodiment of an oxygen separation device according to the invention.

FIG. 4 shows a further embodiment of an arrangement 76. Comparable to FIGS. 2 and 3, the arrangement 76 comprises an oxygen separation membrane 78 and a support structure 80 comprising a plurality of support bars 82. According to FIG. 4, however, the oxygen separation membrane 78 comprises beads 88, or agglomerates, respectively, of adsorbent material. The beads 88 may have a diameter in the range several tens of micrometers.

Figure 5:
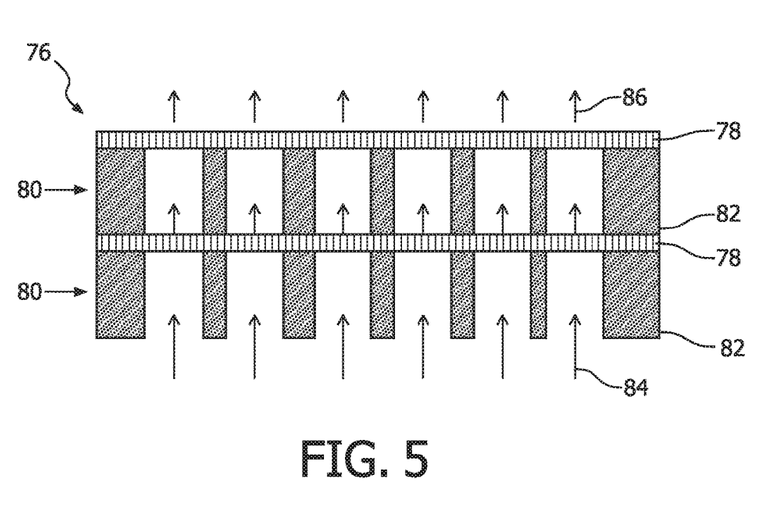
FIG. 5 shows a further embodiment of an oxygen separation device according to the invention.

FIG. 5 shows a further embodiment of an arrangement 76. Comparable to FIGS. 2, 3 and 4, an oxygen separation membrane 78 and a support structure 80 comprising a plurality of support bars 82 is provided. According to FIG. 5, however, a stack of membranes 78 with support bars 82 respectively is provided. According to FIG. 5 two separation membranes 78 are provided, wherein one oxygen separation membrane 78 is located downstream a further oxygen separation membrane 78, and wherein the oxygen separation membranes 78 are connected by a plurality of support bars 82. The stack of membranes 78 and support bars 82 can be fixed on top of each other or alternatively loosely stacked on top of each other.

Figure 6:
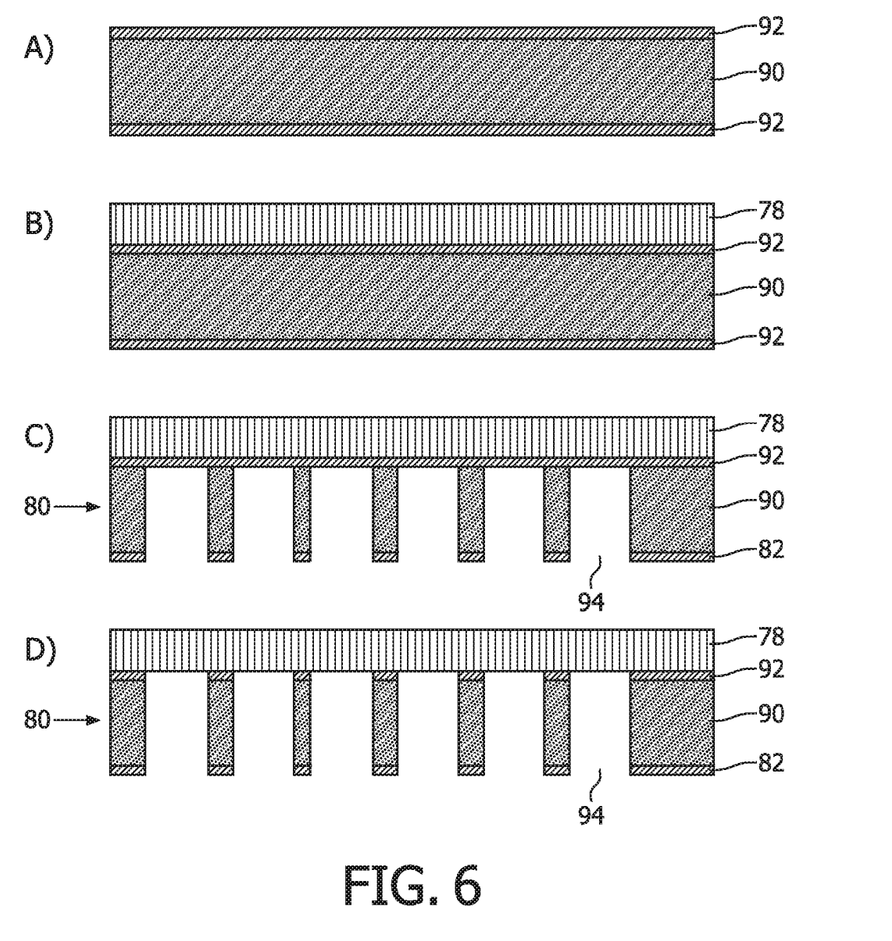
FIG. 6 shows a method for generating an oxygen separation device according to the invention.

A method for generating an arrangement 76, and thus an oxygen separation device 12, 14, respectively, is shown in FIG. 6. The method may start by providing a substrate 90, such as a silicon substrate. The substrate 90 may have a thickness of ≥300 μm to ≤1000 μm, for example. On one or more surfaces of the substrate a further layer 92 comprising silicon dioxide or silicon nitride may be provided, for example having a thickness in the range of ≥50 nm to ≤200 nm. The layer 92 may for example be formed by at least partly oxidizing the substrate, but can also be deposited by e.g. chemical vapor deposition, spin-coating or any other technology. This is shown in step A of FIG. 6.

According to step B of FIG. 6, an oxygen separation membrane 78 is provided onto the substrate, or onto the layer 92, respectively. The membrane 78 may be deposited onto the substrate, for example, by generally known deposition techniques, such as sol-gel processing, spin on processing and/or spray deposition. Also, laser ablation or sputtering processes or hydrothermal processes may be used. Furthermore also printing technologies such as screen printing technologies could be applied.

According to step C of FIG. 6, the layer 92 as well as the substrate 90 is patterned from the backside, i.e. from the opposite side with respect to the membrane 78. By the patterning step, the substrate 90 is processed by forming a plurality of substrate bars 82 out of the substrate 90, having flowing paths 94 there between. In a further step, shown as step D in FIG. 6, the layer 92 adjacent to the membrane 78 is patterned in the same or a comparable manner. The processing, or patterning, respectively of the substrate 90 and the layer 92 may thereby be realized by micro-machining or sandblasting, for example. The resulting structure may comprise support bars with a length of ≥50 μm.

In a slightly modified process flow, the substrate 90 such as a silicon substrate 90 with a potential thickness of ≥300 μm to ≤1000 μm is thinned down e.g. by polishing, to an exemplary thickness in a range of ≥50 μm to ≤300 μm before in step C the substrate 90 is patterned from the backside to realize a plurality of substrate bars, dependent on the desired dimensions of the support bars 82.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. Oxygen separation device for a pressure swing adsorption system, comprising
 a gas inlet at a primary side of the oxygen separation device for guiding a flow of oxygen comprising gas into the oxygen separation device and a gas outlet at a secondary side for guiding a flow of oxygen enriched gas out of the oxygen separation device,
 an oxygen separation membrane comprising an oxygen separation sorbent being capable of separating oxygen from an oxygen comprising gas by sorbing at least one component of the oxygen comprising gas apart from oxygen, and
 a support structure at the primary side of the oxygen separation device, the support structure configured for supporting the oxygen separation membrane, wherein the support structure comprises a plurality of support bars being fixed to the oxygen separation membrane, wherein the plurality of support bars define a flow path for the oxygen comprising gas between the support bars; and the gas inlet is configured to guide flow of oxygen comprising gas to the oxygen separation membrane through the flow path.

2. Oxygen separation device according to claim 1, wherein the oxygen separation sorbent comprises a zeolite material.

3. Oxygen separation device according to claim 1, wherein the support bars comprise silicon, glass, ceramic, glass ceramic, metal, or one or more combinations of one or more of the afore-mentioned materials.

4. Oxygen separation device according to claim 1, wherein a layer is provided at least at one end of the support bars, the layer comprising silicon dioxide, silicon nitride, a combination of the afore-mentioned materials, or a spin-on glass layer.

5. Oxygen separation device according to claim 1, wherein the support bars comprise a porous material.

6. Oxygen separation device according to claim 1, wherein a plurality of oxygen separation membranes is provided, wherein one oxygen separation membrane is located downstream a further oxygen separation membrane.

7. Oxygen separation device according to claim 1, wherein the support bars have a length of ≥50 μm.

8. Oxygen separation device according to claim 1, wherein the oxygen separation membrane has a thickness of ≥1 μm to ≤500 μm.

9. Oxygen separation device according to claim 1, wherein the oxygen separation membrane comprises zeolite crystallites, or zeolite particles, or zeolite beads.

10. Oxygen separation device according to claim 1, wherein the oxygen separation membrane together with the support structure is mounted in a housing.

11. Oxygen separator, comprising
    (a) at least one oxygen separation device comprising a pressure swing adsorption system, comprising:
        (1) a gas inlet at a primary side of the oxygen separation device for guiding a flow of oxygen comprising gas into the oxygen separation device and a gas outlet at a secondary side for guiding a flow of oxygen enriched gas out of the oxygen separation device,
        (2) an oxygen separation membrane comprising an oxygen separation sorbent being capable of separating oxygen from an oxygen comprising gas by sorbing at least one component of the oxygen comprising gas apart from oxygen, and
        (3) a support structure at the primary side of the oxygen separation device, the support structure configured for supporting the oxygen separation membrane, wherein the support structure comprises a plurality of support bars being fixed to the oxygen separation membrane, wherein the plurality of support bars define a flow path for the oxygen comprising gas between the support bars, and wherein the gas inlet is configured to guide flow of oxygen comprising gas to the oxygen separation membrane through the flow path; and
    a pressure adjusting device for creating a pressure difference between the primary side and the secondary side of the oxygen separation device.

12. Oxygen separator according to claim 11, wherein at least two oxygen separation devices are provided, and wherein at least two oxygen separation devices are arranged in parallel.

13. Method of generating an oxygen separation device for a pressure swing adsorption system according to claim 1, comprising the steps of:
    providing a substrate;
    providing an oxygen separation membrane onto the substrate, wherein the oxygen separation membrane comprises an oxygen separation sorbent being capable of separating oxygen from an oxygen comprising gas by sorbing at least one component of the oxygen comprising gas apart from oxygen; and
    processing the substrate by forming a plurality of substrate bars out of the substrate.

14. Method according to claim 13, wherein a layer comprising silicon oxide and silicon nitride or a combination of the afore-mentioned materials, or a spin-on glass layer is applied to at least a part of the substrate.

15. Method according to claim 13, wherein the substrate is processed by micro-machining or sandblasting.

* * * * *